(12) United States Patent
Tinge et al.

(10) Patent No.: US 10,301,243 B2
(45) Date of Patent: May 28, 2019

(54) PROCESS FOR THE PRODUCTION OF CYCLOHEXANONE FROM PHENOL

(71) Applicant: CAP III B.V., Urmond (NL)

(72) Inventors: Johan Thomas Tinge, Sittard (NL); Corinne Daguenet, Echt (NL); Iris Verschuren, Sittard (NL); Wilhelmus Rudolf Maria Martens, Sittard (NL); Roeland Wilhelmus Theodorus Maria Brands, Echt (NL); Robert Jan de Korte, Echt (NL)

(73) Assignee: CAP III B.V., Urmond (NL)

( * ) Notice: Subject to any disclaimer, the term of this patent is extended or adjusted under 35 U.S.C. 154(b) by 0 days.

(21) Appl. No.: 15/525,448

(22) PCT Filed: Nov. 6, 2015

(86) PCT No.: PCT/EP2015/075951
§ 371 (c)(1),
(2) Date: May 9, 2017

(87) PCT Pub. No.: WO2016/075047
PCT Pub. Date: May 19, 2016

(65) Prior Publication Data
US 2018/0290955 A1 Oct. 11, 2018

(30) Foreign Application Priority Data

Nov. 10, 2014 (EP) .................................. 14192423
Oct. 29, 2015 (WO) ................. PCT/EP2015/075113

(51) Int. Cl.
*C07C 45/82* (2006.01)
*C07C 45/00* (2006.01)
*C07C 29/20* (2006.01)
*C07C 29/80* (2006.01)

(52) U.S. Cl.
CPC ............ *C07C 45/006* (2013.01); *C07C 29/20* (2013.01); *C07C 29/80* (2013.01); *C07C 45/002* (2013.01); *C07C 45/82* (2013.01); *C07C 2601/14* (2017.05)

(58) Field of Classification Search
CPC .............................. C07C 45/006; C07C 45/82
See application file for complete search history.

(56) References Cited

U.S. PATENT DOCUMENTS

| | | | |
|---|---|---|---|
| 2,829,166 | A | 4/1958 | Joris et al. |
| 5,015,787 | A | 5/1991 | Van Peppen |
| 8,618,334 | B2 | 12/2013 | Horsels et al. |
| 9,388,107 | B2 | 7/2016 | Martens et al. |
| 2011/0028675 | A1 | 2/2011 | Van Dortmont et al. |
| 2011/0028763 | A1 | 2/2011 | Parton et al. |
| 2011/0054142 | A1 | 3/2011 | Horsels et al. |
| 2016/0368844 | A1 | 12/2016 | Dakka et al. |
| 2017/0233323 | A1 | 8/2017 | Becker et al. |

FOREIGN PATENT DOCUMENTS

| | | |
|---|---|---|
| WO | 2009080618 A1 | 7/2009 |
| WO | 2309080621 A1 | 7/2009 |
| WO | 2014/001461 | 1/2014 |

OTHER PUBLICATIONS

International Search Report for PCT/EP2013/063529 dated Sep. 6, 2013.
Dimian, Alexandre C., et al. "Phenol Hydrogenation to Cyclehexanone," Chemical Process Design: Computer-Aided Cases Studies, Mar. 3, 2008, DOI: 10.1002/9783527621583.ch5.

*Primary Examiner* — Sikarl A Witherspoon
(74) *Attorney, Agent, or Firm* — Honigman LLP; Fernando Alberdi; Jonathan P. O'Brien

(57) ABSTRACT

An industrial scale continuous process for the production and recovery of cyclohexanone from phenol and hydrogen, said process comprising: hydrogenating phenol in a phenol hydrogenation reactor; separating cyclohexanone from a hydrogenated product stream in a separation and purification section [II] comprising at least 4 distillation sections; wherein at least some of the reaction heat produced in the phenol hydrogenation reaction section [I] is applied for the production of steam; and wherein the molar ratio of cyclohexanone to phenol that is charged to said phenol hydrogenation reactor is from 0.02 to 0.10; and/or wherein the molar ratio of cyclohexanol to phenol that is charged to said phenol hydrogenation reactor is from 0.001 to 0.10.

14 Claims, 4 Drawing Sheets

PROCESS FOR THE PRODUCTION OF CYCLOHEXANONE FROM PHENOL

CROSS-REFERENCE

This application is a 35 U.S.C. § 371 national phase filing claiming the benefit of and priority to Patent Cooperation Treaty application no. PCT/EP2015/075951, filed Nov. 6, 2015, which claims the benefit of and priority to Patent Cooperation Treaty application no. PCT/EP2015/075113, filed Oct. 29, 2015 and EP patent application no. 14192423.3, filed on Nov. 10, 2014, the entire contents of the aforementioned disclosures are hereby incorporated by reference herein.

The invention relates to a continuous process for the preparation of cyclohexanone from phenol on an industrial scale and to a chemical plant suitable for carrying out the process according to the invention on an industrial scale.

The vast majority of cyclohexanone is consumed in the production of caprolactam, which is an intermediate in the manufacture of nylon 6. Mixtures of cyclohexanone and cyclohexanol are used for the production of adipic acid, which is mainly converted into nylon 6,6. In addition cyclohexanone can be employed as an industrial solvent or as an activator in oxidation reactions. It can also be used as an intermediate for the production of cyclohexanone resins.

In the 1930's the production of cyclohexanone started on an industrial scale, in parallel with the commercial production of caprolactam and nylon 6. Ever since the production volume of cyclohexanone has been growing and nowadays the annual production of cyclohexanone is over 6 million tons.

By industrial scale is meant a production rate of at least 1,000 kg of cyclohexanone per hour, more preferably at least 5,000 kg of cyclohexanone per hour and most preferably at least 10,000 kg of cyclohexanone per hour.

Cyclohexanone is conventionally prepared from phenol by catalytic hydrogenation in a phenol hydrogenation reactor, e.g. using a platinum or a palladium catalyst. The reaction can be carried out in the liquid phase or the vapour phase. [Kirk-Othmer Encyclopedia of Chemical Technology, e.g. 3rd Edition, Vol. 7 (1979) p. 410-416; I. Dodgson et al. "A low Cost Phenol to Cyclohexanone Process", Chemistry & Industry, 18, December 1989, p. 830-833; or M T. Musser "Cyclohexanol and Cyclohexanone", Ullmann's Encyclopedia of Industrial Chemistry (7th Edition, 2007), (hereafter "Musser").

The process for the hydrogenation of phenol to the two major products, cyclohexanone and cyclohexanol, can be described by the following stoichiometric equations:

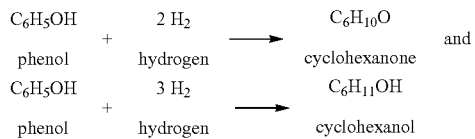

In conventional processes generally a compromise has to be made between the yield of the desired product (cyclohexanone and/or cyclohexanol formed as a percentage of the phenol feed), and the selectivity of the reaction (cyclohexanone and/or cyclohexanol formed as a percentage of phenol that has been converted). As described in the above identified publications several factors play a role herein, including temperature, choice of catalyst, and the hydrogen/phenol feed ratio.

A conventional process for the preparation and recovery of cyclohexanone from phenol feedstock is described in Musser or in U.S. Pat. No. 3,305,586. Such a process consists of two or optionally three sections. Cyclohexanone is prepared in a phenol hydrogenation reaction section. In the phenol hydrogenation reaction section a fresh phenol stream is hydrogenated in a vapour phase process or in a liquid phase process. From this phenol hydrogenation reaction section a gaseous purge stream comprising hydrogen and optionally inerts like nitrogen and/or methane, and a phenol hydrogenation reaction section product stream comprising cyclohexanone and cyclohexanol, phenol and side-products are discharged. In a separation and purification section cyclohexanone is separated from the phenol hydrogenation reaction section product stream. Optionally co-produced cyclohexanol is converted to cyclohexanone in a cyclohexanol dehydrogenation reaction section.

The process for the dehydrogenation of cyclohexanol to cyclohexanone can be described by the following stoichiometric equation:

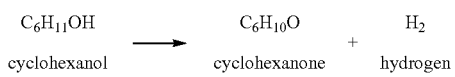

Generally, this endothermic dehydrogenation reaction is performed in the gas phase. Several catalysts can be applied for this dehydrogenation reaction including catalysts based on copper and/or zinc, including catalysts comprising $CuCrO_4 2CuO \cdot 2H_2O$, CuMgO, CuZnO, CuCrO, CuCrMnV and ZnO.

The cyclohexanone is typically recovered by a distillation process as a product rich in cyclohexanone (usually very rich 90 wt. %) or as an essentially pure product 99 wt. %). For the production of high grade nylon, a purity of at least 99.5 wt. % and more preferably at least 99.8 wt. % of cyclohexanone is desired.

In 2008 Alexandre C. Dimian and Costin Sorin Bildea (Chapter 5: "Phenol Hydrogenation to Cyclohexanone" in "Chemical Process Design: Computer-Aided Case Studies", 2008, Wiley-VCH Verlag GmbH & Co. KGA, Weinheim, ISBN: 978-3-527-31403-4) reported an overall steam consumption for the phenol hydrogenation reaction section and the separation and purification section of 1.40 kg steam per kg product. In addition the cyclohexanol dehydrogenation reaction section required 0.49 MJ heat of a high temperature per kg product (2010 kW heat for a production of 4.1 kg product per second). In their case the product was cyclohexanone with a purity of 98 mol %.

So, in their case the production of cyclohexanone from phenol required 1.40 kg steam per kg product plus 0.49 MJ heat per kg product.

From these figures the net energy consumption of their process can be calculated after converting the presented steam consumption figure into an energy consumption figure. A. C. Dimian et al. give on page 158 (line 9) for the enthalpy of vaporization of water into steam a value of 2.083 MJ/kg steam. By using this value the net energy consumption of their process can be expressed as being about 3.4 MJ (=1.40*2.083+0.49) per kg product. In the event that the 0.49 MJ heat per kg product that is required in their process is supplied by steam heating, it is also possible to calculate the net steam consumption of their process. Then the net steam consumption of their process is about 1.6 kg (=1.40+ 0.49/2.083) steam per kg product. It should be noted that the energy integration study performed by A. C. Dimian et al. is based on a flowsheet for liquid-separation by indirect sequencing in which the phenol azeotrope is not distilled overhead.

A problem with the prior art is that the net energy consumption for the production of pure cyclohexanone from phenol per kg of product is high and may easily be above 3 MJ heat per kg product. And in the event that all the heat is supplied by steam, the net steam consumption may be easily above 1.5 kg steam per kg of product. A high net consumption of heat per kg of product and/or a high net consumption of steam per kg of product does not just have a negative impact on the carbon foot print of the process, but has also a negative impact on the variable costs of cyclohexanone production. An additional problem with the prior art is that the obtained product has a purity of just 98 mol %, which is equivalent to almost 98 wt. %, because cyclohexanol is the major impurity in the product. Additional purification of the obtained product to a product with a purity of 99.5 wt. % or even 99.95 wt. % will even further increase the net consumption of heat per kg of product and/or net consumption of steam per kg of product.

It is therefore an object of the present invention to provide a process on an industrial scale for preparing pure cyclohexanone, wherein the above drawbacks are overcome or at least alleviated.

It is therefore an object of the present invention to provide a process for preparing pure cyclohexanone with an purity of at least 99.5 wt. % that has a net energy consumption per kg of product that is lower than what is known. The cyclohexanone produced with such a process will have an improved carbon foot print and the variable costs of the produced cyclohexanone will be reduced. In addition the produced cyclohexanone meets the specifications required for the production of high grade nylon.

The aforementioned shortcomings are solved in the current invention where a reduced net energy consumption per kg of product and/or net steam consumption per kg of product is combined with the production of a product with an increased purity for a process in which at least 98% (mol/mol) of the supplied fresh phenol is converted into product (cyclohexanone). Preferably, even more than 99% (mol/mol) of the supplied fresh phenol is converted into product. Even more preferably, even more than 99.5% (mol/mol) of the supplied fresh phenol is converted into product.

The net energy consumption per kg of product is reduced by the following combination of I) a high per-pass phenol conversion in the phenol hydrogenation reaction section; II) a high cyclohexanone to cyclohexanol ratio in the reaction mixture leaving the phenol hydrogenation reaction section; III) a high per pass selectivity towards cyclohexanone in the phenol hydrogenation reaction section; and IV) a high degree of heat integration in the process for the production, recovery and purification of cyclohexanone and optionally in the process for the dehydrogenation of cyclohexanol. The purity of the product has been increased by implementing a distillation section with an increased purification efficiency.

Therefore, according to the invention there is provided an industrial scale continuous process for the production and recovery of cyclohexanone from phenol and hydrogen, said process comprising:
I) hydrogenating phenol in a phenol hydrogenation reactor in a phenol hydrogenation reaction section [I] with gaseous hydrogen, in the presence of platinum and/or palladium comprising catalyst, whereby reaction heat is produced and from which a hydrogenated product stream is discharged;
II) separating cyclohexanone from said hydrogenated product stream in a separation and purification section [II] by multiple-steps comprising:
   i. removing in a first distillation section, components with a boiling point lower than cyclohexanone;
   ii. removing in a second distillation section cyclohexanone;
   iii. removing in a third distillation section a cyclohexanol rich phase; and
   iv. removing in a fourth distillation section a mixture comprising phenol and cyclohexanol;
wherein said cyclohexanone has a cyclohexanol content below 5000 ppm (weight/weight);
wherein at least some of the reaction heat produced in the phenol hydrogenation reaction section [I] is applied for the production of steam; and
wherein the mixture comprising phenol and cyclohexanol that is removed in step iv) is charged to the phenol hydrogenation reaction section [I];
characterized in that at least one of conditions a) or b) applies:
   a. the molar ratio of cyclohexanone to phenol that is charged to said phenol hydrogenation reactor is from 0.02 to 0.10;
   b. the molar ratio of cyclohexanol to phenol that is charged to said phenol hydrogenation reactor is from 0.001 to 0.10.

Preferably, the molar ratio of cyclohexanone to phenol that is charged to said phenol hydrogenation reactor is from 0.02 to 0.08; more preferably from 0.03 to 0.07; yet more preferably from 0.03 to 0.05; for example about 0.04.

Preferably, the molar ratio of cyclohexanol to phenol that is charged to said phenol hydrogenation reactor is from 0.002 to 0.05; more preferably from 0.003 to 0.04; for example about 0.01.

Preferably the molar ratio of cyclohexanone to phenol that is charged to said phenol hydrogenation reactor is from 0.02 to 0.10, and the molar ratio of cyclohexanol to phenol that is charged to said phenol hydrogenation reactor is from 0.001 to 0.10.

Preferably the process further comprises dehydrogenating cyclohexanol into cyclohexanone and hydrogen in a cyclohexanol dehydrogenation reaction section [III]. Preferably hydrogen produced in the cyclohexanol dehydrogenation reaction section [III] is charged to the phenol hydrogenation reaction section [I].

Preferably the molar ratio of cyclohexanone over cyclohexanol in the hydrogenated product stream discharged in step I) is greater than 10. More preferably, the molar ratio of cyclohexanone over cyclohexanol in the hydrogenated product stream discharged in step I) is greater than 20; yet more preferably greater than 40; most preferably greater than 80. Preferably the molar ratio of cyclohexanone over phenol in the hydrogenation product stream discharged in step I) is greater than 10. More preferably the molar ratio of cyclohexanone over phenol in the hydrogenation product stream discharged in step I) is greater than 20; yet more preferably greater than 40; most preferably greater than 80.

In the process of the present invention, in step II), preferably each independently of i, ii, ii and iv involves removing the specified product overhead. The process of the present invention, in step II), preferably involves: i. removing overhead in a first distillation section, components with a boiling point lower than cyclohexanone. The process of the present invention, in step II), preferably involves: ii. removing overhead in a second distillation section cyclohexanone. The process of the present invention, in step II), preferably involves: iii. removing overhead in a third distillation section a cyclohexanol rich phase. The process of the present invention, in step II), preferably involves: iv. removing overhead in a fourth distillation section a mixture comprising phenol and cyclohexanol. Accordingly, preferably, according to the invention there is provided an industrial scale continuous process for the production and recovery of cyclohexanone from phenol and hydrogen, said process comprising:

I) hydrogenating phenol in a phenol hydrogenation reactor in a phenol hydrogenation reaction section [I] with gaseous hydrogen, in the presence of platinum and/or palladium comprising catalyst, whereby reaction heat is produced and from which a hydrogenated product stream is discharged;

II) separating cyclohexanone from said hydrogenated product stream in a separation and purification section [II] by multiple-steps comprising:
  i. removing overhead in a first distillation section, components with a boiling point lower than cyclohexanone;
  ii. removing overhead in a second distillation section cyclohexanone;
  iii. removing overhead in a third distillation section a cyclohexanol rich phase; and
  iv. removing overhead in a fourth distillation section a mixture comprising phenol and cyclohexanol;

wherein said cyclohexanone has a cyclohexanol content below 5000 ppm (weight/weight);
wherein at least some of the reaction heat produced in the phenol hydrogenation reaction section [I] is applied for the production of steam; and
wherein the mixture comprising phenol and cyclohexanol that is removed overhead in step iv) is charged to the phenol hydrogenation reaction section [I];
characterized in that at least one of conditions a) or b) applies:
  a. the molar ratio of cyclohexanone to phenol that is charged to said phenol hydrogenation reactor is from 0.02 to 0.10;
  b. the molar ratio of cyclohexanol to phenol that is charged to said phenol hydrogenation reactor is from 0.001 to 0.10.

The first distillation section is followed by the second distillation section, which is followed by the third distillation section, which is followed by the fourth distillation section. Preferably, the first distillation section is followed directly by the second distillation section, which is followed directly by the third distillation section, which is followed directly by the fourth distillation section.

According to the present invention cyclohexanone as removed in the second distillation section is defined as comprising less than 5000 ppm (weight/weight) cyclohexanol, more preferably less than 4000 ppm (weight/weight) cyclohexanol, yet more preferably less than 3000 ppm (weight/weight) cyclohexanol, further preferably less than 2000 ppm (weight/weight) cyclohexanol, and most preferably less than 1000 ppm (weight/weight) cyclohexanol. For clarity 2000 ppm (weight/weight) of cyclohexanol is 0.2 wt. % cyclohexanol.

The purity of cyclohexanone is defined as being 100% minus the content of cyclohexanol. So, in this definition impurities other than cyclohexanol are neglected.

Cyclohexanone that comprises 2000 ppm (weight/weight) of cyclohexanol, which is 0.2 wt. % cyclohexanol, has a purity of 99.8 wt. %.

Preferably, the resultant cyclohexanone has a purity of at least 99.8 wt. %.

According to the invention preferably at least more than 30%, more preferably more than 40%, yet more preferably more than 50%, further preferably more than 65%, still more preferably more than 80% and most preferably more than 90% of the reaction heat produced in the phenol hydrogenation reaction section is applied for the production of steam. This production of steam may be for use in the process of invention or may be used for other applications. Preferably, the steam produced is used to transfer energy to drive one or more reboilers in the various distillation sections or to the cyclohexanol dehydrogenation reaction section, or both.

The resultant hydrogenated product stream comprises phenol, hydrogen, inerts and hydrogenated phenol.

Preferably phenol is hydrogenated in a vapour phase process.

The per-pass phenol conversion in a continuous operating phenol hydrogenation reaction section is defined as $(phenol^{in} - phenol^{out})/phenol^{in}$, whereby $phenol^{in}$ is the flow rate of phenol that is charged to the phenol hydrogenation reaction section, expressed in mol/s, and $phenol^{out}$ is the flow rate of the phenol that is discharged from the phenol hydrogenation reaction section, expressed in mol/s.

The per-pass selectivity in a continuous operating phenol hydrogenation reaction section is defined as $(cyclohexanone^{out} - cyclohexanone^{in})/(phenol^{in} - phenol^{out})$, whereby $cyclohexanone^{in}$ is the flow rate of cyclohexanone that is charged to the phenol hydrogenation reaction section, expressed in mol/s, $cyclohexanone^{out}$ is the flow rate of the cyclohexanone that is discharged from the phenol hydrogenation reaction section, expressed in mol/s, $phenol^{in}$ is the flow rate of phenol that is charged to the phenol hydrogenation reaction section, expressed in mol/s, and $phenol^{out}$ is the flow rate of the phenol that is discharged from the phenol hydrogenation reaction section, expressed in mol/s.

Preferably the per-pass selectivity in the phenol hydrogenation reaction section is greater than 90%. More preferably it is greater than 91%, for example greater than 92%, 93%, 94%, 95% or 96%.

Preferably the per-pass phenol conversion in the phenol hydrogenation reaction section is greater than 86%. More preferably it is greater than 88%; for example greater than 90%, 92%, 94%, 96%.

A cyclohexanol rich phase is defined as a phase with a cyclohexanol content of more than 50 wt. %, preferably more than 75 wt. % and even more preferably more than 85 wt. %.

A cyclohexanone rich organic phase is defined as a phase with a cyclohexanone content of more than 98 wt. %, preferably more than 99 wt. % and even more preferably more than 99.5 wt. %.

The cyclohexanone is economically produced with high conversion of phenol, high product selectivity, high final product purity and a reduced net energy consumption.

In the phenol hydrogenation reaction section cyclohexanone and cyclohexanol are obtained in a continuous process by catalytically hydrogenation of phenol. The applied hydrogenation catalyst may in principle be any (supported) hydrogenation catalyst capable of catalyzing the hydrogenation of phenol. Usually, the (supported) hydrogenation catalyst comprises one or more catalytically active metals and comprises a promoter. Such metal or metals may in particular be selected from the group of palladium, platinum, ruthenium, rhodium, iridium, rubidium and osmium. Palladium, platinum or a combination thereof are preferred catalytically active metals, in particular for the hydrogenation of phenol, especially for the hydrogenation into cyclohexanone or a mixture of cyclohexanone and cyclohexanol, wherein the cyclohexanone is the major component of these two. In principle any support may be used that is suitable for use in the hydrogenation of the compound of interest, in combination with the catalytic material it supports. Suitable supports in particular may be selected from the group of alumina, activated carbon, titanium oxide, calcium carbonate and carbon black. Another support that may be used is silica. Particularly preferred for a good stability of the support under reaction conditions and/or an improved conversion is a support selected from the group of alumina and activated carbon.

Alumina is particularly preferred as support for an embodiment wherein the phenol to be hydrogenated is fed into the reactor as a vapour.

Activated carbon is particularly preferred as support for an embodiment wherein the phenol to be hydrogenated are fed into the reactor as a liquid.

Preferably, the applied hydrogenation catalyst is a supported catalyst, comprising a promoter comprising an alkali metal or alkaline earth metal salt. Preferably, the applied hydrogenation catalyst is a supported catalyst, comprising a promoter selected from the group of alkali metal hydroxides, alkaline earth metal hydroxides, alkaline earth metal oxides, (bi)carbonates of alkali metals and (bi)carbonates of alkaline earth metals.

Promoters are added to increase the activity lifetime and the selectivity to the desired product of the catalyst. A short life time i.e., high deactivation rate, means high frequency of interruption of the process to regenerate or replace the catalyst, of course, reducing operating times and increasing costs. A lower selectivity means that a larger fraction of the phenol is converted into products other than cyclohexanone.

A more preferred catalyst/support/promoter combination is palladium on alumina support. Optionally, Na in the form of $NaHCO_3$ is added as promoter.

The most preferred catalyst/support/promoter combination is 1 wt. % palladium on alumina support, with 1 wt. % Na (as $NaHCO_3$) added as promoter.

The hydrogenation reactor used in the phenol hydrogenation reaction section may be any type of reactor suitable for hydrogenation of the compound to be hydrogenated, in particular any reactor suitable for the hydrogenation of phenol. For example, the reactor may be selected from packed bed reactors, slurry reactors, shell and tubes heat exchange reactors with catalyst in tubes and with generation of steam, and any other suitable type of reactor. Most preferably, the hydrogenation according to the invention is carried out in a shell and tubes heat exchange reactor. Most preferably, in such a shell and tubes heat exchange reactor, the tubes are filled with a supported catalyst. Most preferably, such a shell and tubes heat exchange reactor is fed with water, e.g. boiler feed water or condensate, to the volume outside the tubes for removal of reaction heat, whereby steam is produced. Optionally, this steam that is produced is used for heating purposes.

The separation and purification section usually comprises a number of distillation sections. A distillation section, as used herein is an installation comprising one distillation column or a plurality of distillation columns in parallel, each having the same functionality, some of which may be vacuum distillation columns. Further this section may comprise other typical parts of distillation units, such as reboilers and condensers.

The net energy consumption of a process, expressed in MJ per kg of produced cyclohexanone, is defined as the sum of the energy consumed by the energy consumers minus the sum of the energy produced by the energy producers. Energy consumers are defined as process steps in which heat from outside the process step is charged to the process step via one or more heat exchangers. Energy producers are defined as process steps in which heat from inside the process step is discharged from a process step via one or more heat exchangers.

The net steam consumption, expressed in kg steam per kg of produced cyclohexanone, is defined as the sum of the steam consumed by the steam consumers minus the sum of the steam produced by the steam producers. Steam consumers are defined as process steps in which steam from outside the process step is charged to the process step via one or more heat exchangers. Steam producers are defined as process steps in which steam from inside the process step is discharged from a process step via one or more heat exchangers.

Preferably in the present invention, to reach a cyclohexanone purity of 99.5 wt. %, the net energy consumption expressed in MJ per kg produced cyclohexanone is less than 3 MJ/kg produced cyclohexanone. More preferably it is less than 2.5 MJ/kg produced cyclohexanone, for example less than 2 MJ/kg or less than 1.7 MJ/kg.

Preferably in the present invention, to reach a cyclohexanone purity of 99.5 wt. % the net steam consumption, expressed in kg steam per kg produced cyclohexanone is less than 1.5 kg steam per kg produced cyclohexanone. More preferably it is less than 1.0 kg steam per kg produced cyclohexanone, for example less than 0.8 kg steam/kg.

The net energy consumption of a process can also be expressed in kg steam per kg produced cyclohexanone. As a conversion factor the (average) enthalpy of vaporization of water into steam, expressed in MJ/kg steam, should be used, which is known to a person skilled in the art.

In a further embodiment of the invention there is provided an industrial scale continuous chemical plant for the production and recovery of cyclohexanone from phenol and hydrogen, said plant comprising:

I) a phenol hydrogenation reaction section [I] comprising a phenol hydrogenation reactor in which phenol is hydrogenated with gaseous hydrogen, in the presence of platinum- and/or palladium-comprising catalyst, whereby reaction heat is produced and from which a hydrogenated product stream is discharged;

II) a separation and purification section [II] in which cyclohexanone is separated from said hydrogenated product stream by multiple-steps comprising:
  i. a first distillation section, in which components with a boiling point lower than cyclohexanone are removed;
  ii. a second distillation section, in which cyclohexanone is removed;
  iii. a third distillation section, in which a cyclohexanol rich phase is removed; and
  iv. a fourth distillation section, in which a mixture comprising phenol and cyclohexanol is removed;
wherein said cyclohexanone has a cyclohexanol content below 5000 ppm (weight/weight);

wherein at least some of the reaction heat produced in the phenol hydrogenation reaction section [I] is applied for the production of steam; and wherein the mixture comprising phenol and cyclohexanol that is removed in step iv) is charged to the phenol hydrogenation reaction section [I];

characterized in that at least one of conditions a) or b) applies:

a. the molar ratio of cyclohexanone to phenol that is charged to said phenol hydrogenation reactor is from 0.02 to 0.10;

b. the molar ratio of cyclohexanol to phenol that is charged to said phenol hydrogenation reactor is of from 0.001 to 0.10.

Typically, the phenol hydrogenation reaction section [I] comprises:

steam heated heat exchanger section [a], for heating a feed of fresh phenol;

steam heated evaporation section [b], for evaporating phenol;

steam heated heat exchanger section [c], for heating a feed of fresh hydrogen;

hydrogen purification unit [d], for purifying a feed of fresh hydrogen by catalytically converting CO, and removing $H_2S$ by an adsorbent;

steam heated heat exchanger section [e], for heating a feed of evaporated phenol and hydrogen gas;

phenol hydrogenation section [f], for gas-phase hydrogenation of phenol and generation of steam from cooling water, heat exchanger section [g], for transfer of heat from phenol hydrogenation product stream to a hydrogen recycle feed;

heat exchanger section [h], for recovering heat from the phenol hydrogenation product stream;

water cooled heat exchanger section [i], for cooling the phenol hydrogenation product stream;

gas-liquid separation section [j], for separating hydrogen gas from the phenol hydrogenation product stream;

compression section [k], for compressing separated hydrogen gas; and (optionally) heat exchanger section [m] for cooling compressed hydrogen gas.

Preferably, the phenol hydrogenation section [I] comprises one or more shell and tube type hydrogenation reactors for phenol hydrogenation in the vapour phase which are, in case of two or more, operated in parallel and water is used as coolant was evaporated to form steam.

Preferably, heat exchanger section [h] is for recovering heat from the phenol hydrogenation product stream and transferring it to a cyclohexanol dehydrogenation section.

DETAILED DESCRIPTION OF THE DRAWINGS

Figure 1:
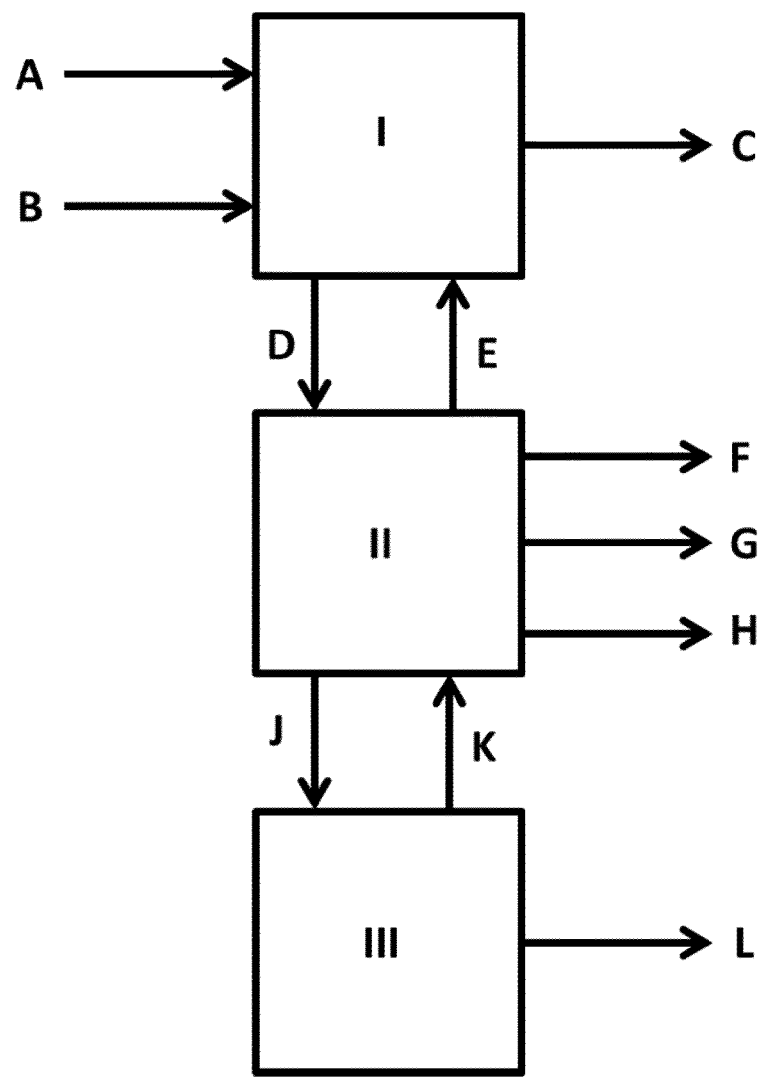
FIG. 1 illustrates schematically a process for the preparation and recovery of cyclohexanone from phenol according to the invention.

A process for the preparation and recovery of cyclohexanone from phenol is schematically shown in FIG. 1. Such a process usually consists of two sections with an optional third section. All three sections are shown.

Cyclohexanone is prepared in phenol hydrogenation reaction section [I].

In separation and purification section [II] cyclohexanone is recovered.

In optional cyclohexanol dehydrogenation reaction section [III] cyclohexanol is catalytically converted into cyclohexanone and hydrogen.

This phenol hydrogenation reaction section [I] in particular comprises a hydrogenation reactor (which during use is supplied with a hydrogen stream via duct [A], a fresh phenol stream via duct [B] and a stream comprising recycled phenol via duct [E]) and may comprise additional equipment. See for instance FIG. 1 in Musser, or in U.S. Pat. No. 3,305,586. The hydrogenation may either take place in a vapour phase process or in a liquid phase process. From this phenol hydrogenation reaction section [I] a gaseous purge stream comprising hydrogen and optionally inerts like nitrogen and/or methane is discharged via duct [C], and a phenol hydrogenation reaction section product stream comprising cyclohexanone, phenol and side-products, such as cyclohexanol is discharged via duct [D]. The phenol hydrogenation reaction section product stream is supplied via duct [D] to separation and purification section [II]. In a separation and purification section [II] cyclohexanone, phenol and side-products, such as cyclohexanol, are usually recovered. Optionally, a cyclohexanol dehydrogenation reaction section [III] product stream comprising cyclohexanol and cyclohexanone is supplied via duct [K] to separation and purification section [II], for further recovery of cyclohexanone and side-products, such as cyclohexanol.

From this separation and purification section [II] a stream comprising recycled phenol is discharged via duct [E], a light components stream, optionally comprising benzene, cyclohexane and water, is discharged via duct [F], a cyclohexanone stream is discharged via duct [G], a heavy components stream comprising phenol and higher boiling components is discharged via duct [H], and a cyclohexanol comprising stream is discharged via duct [J]. Optionally, the cyclohexanol comprising stream is supplied via duct [J] to cyclohexanol dehydrogenation reaction section [III]. Optionally, the cyclohexanol comprising stream is discharged from the process for the preparation and recovery of cyclohexanone from phenol feedstock and used as such or supplied to another process (not shown in FIG. 1).

A cyclohexanol dehydrogenation reaction section [III] usually comprises a dehydrogenation reactor and one or more heat exchangers. In the cyclohexanol dehydrogenation reaction section cyclohexanol is catalytically converted into cyclohexanone and hydrogen. In general the dehydrogenation of cyclohexanol is a gas phase reaction that is performed at temperatures above 200° C. Optionally, the cyclohexanol dehydrogenation reaction section product stream comprising cyclohexanol and cyclohexanone is supplied via duct [K] to separation and purification section [II]. The produced hydrogen in cyclohexanol dehydrogenation reaction section [III] is discharged via duct [L]. Optionally, the produced hydrogen in cyclohexanol dehydrogenation reaction section [III] is supplied to phenol hydrogenation reaction section [I] (not shown in FIG. 1). Optionally, the produced hydrogen in cyclohexanol dehydrogenation reaction section [III] is supplied to another hydrogen consuming process (not shown in FIG. 1). Optionally, the produced hydrogen in cyclohexanol dehydrogenation reaction section [III] is supplied to a heat generation unit (not shown in FIG. 1).

Figure 2:
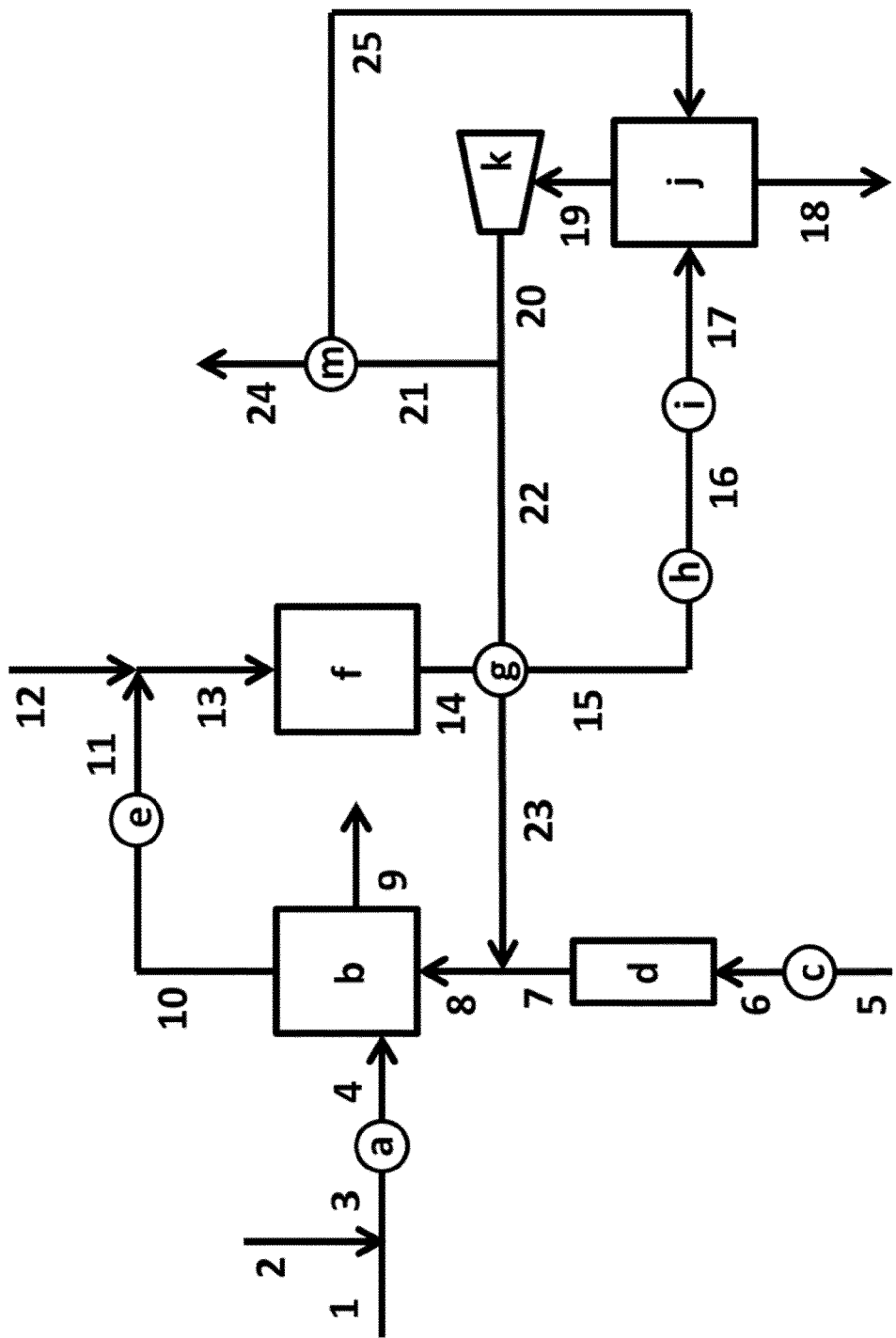
FIG. 2 illustrates schematically an embodiment of a phenol hydrogenation reaction section [I] according to the invention.

In FIG. 2 a scheme of an embodiment according to the invention of a phenol hydrogenation reaction section [I] is given.

A fresh phenol stream is charged via duct [1] and a stream comprising recycled phenol is charged via duct [2], thereby forming a combined stream that flows via duct [3]. The stream comprising recycled phenol that is charged via duct [2] is discharged from the separation and purification section [II] (duct [E] in FIG. 1; duct [2] in FIG. 3). The combined stream that flows via duct [3] is heated in a heat exchanger section [a] and the obtained heated stream is discharged via duct [4] and charged to evaporation section [b]. Heat exchanger section [a] comprises one or more heat exchangers that are operated in parallel and/or in series. Optionally, heat exchanger [a] is absent or by-passed (not shown in FIG. 2).

Fresh hydrogen gas is charged via duct [5] to the phenol hydrogenation reaction section [I]. In general the fresh hydrogen originates from a naphtha cracker, a methane reformer or an electrolysis process. In general the fresh hydrogen gas contains inert components like nitrogen and/or methane. In case the fresh hydrogen contains harmful components, like CO and/or $H_2S$, then a hydrogen gas purification step is required. The presence of these harmful components in the fresh hydrogen can be temporary, e.g. due to upset conditions in the fresh hydrogen gas production unit, or can be permanent. In such a hydrogen purification step the harmful impurities can be converted into inert components or removed from the fresh hydrogen stream.

Fresh hydrogen gas is charged via duct [5] to heat exchanger section [c]. In heat exchanger section [c] the temperature of the fresh hydrogen gas is modified to a temperature required in hydrogen purification unit [d]. In general, in heat exchanger section [c] the temperature of the fresh hydrogen gas is increased. The temperature modified fresh hydrogen gas is discharged from heat exchanger section [c] via duct [6] and charged to hydrogen purification section [d]. Heat exchanger section [c] comprises one or more heat exchangers that are operated in parallel and/or in series. Optionally, heat exchanger section [c] is absent or by-passed (not shown in FIG. 2). Hydrogen purification section [d] might comprise one or more catalysts for the conversion of harmful components into inert components and/or one or more adsorbents for the removal of harmful components. In general hydrogen purification section [d] comprises a catalyst for conversion of CO and/or an adsorbent for the removal of $H_2S$. Hydrogen gas is discharged from hydrogen purification section [d] via duct [7]. The hydrogen gas in duct [7] and the recycled hydrogen gas in duct [23] are combined, thereby forming a stream that flows via duct [8], that is charged to evaporation section [b]. Hydrogen purification section [d] comprises one or more reaction and/or adsorption units that are operated in parallel and/or in series. Optionally, hydrogenation section [d] is absent or by-passed (not shown in FIG. 2).

In evaporation section [b] virtually all components that entered via duct [4] and via duct [8] are evaporated. A stream of gaseous components is discharged from evaporation section [b] via duct [10]. A small amount of the components that entered via duct [4] and via duct [8] is not evaporated and is discharged (either continuously or batch wise) from evaporation section [b] via duct [9]. In general evaporation section [b] is steam heated. In general evaporation section [b] comprises a device, e.g. a wire-mesh demister, for removal of entrained droplets from the stream of gaseous components that is discharged. Evaporation section [b] comprises one or more evaporators that are operated in parallel and/or in series. Optionally, the stream of gaseous components in duct [10] is temperature adjusted in heat exchanger section [e]. In general in heat exchanger section [e] the stream of gaseous components is raised in temperature. The temperature adjusted stream discharges heat exchanger section [e] via duct [11]. Heat exchanger section [e] comprises one or more heat exchangers that are operated in parallel and/or in series. Optionally, some water, e.g. in the form of vapor, is added via duct [12] to the stream in duct [11] and thereby forming a stream that flows via duct [13], that is charged to phenol hydrogenation section [f]. Phenol hydrogenation section [f] consists of one or more hydrogenation reactors that are operated in series and/or in parallel. In phenol hydrogenation section [f] cyclohexanone and cyclohexanol are obtained in a continuous process by catalytical hydrogenation of phenol.

For clarity the phenol hydrogenation section [f] is one of the sections within phenol hydrogenation reaction section [I].

A gas mixture comprising hydrogen, phenol, cyclohexanone and cyclohexanol is discharged from phenol hydrogenation section [f] via duct [14]. In heat exchanger section [g] this gas mixture is heat exchanged with a hydrogen comprising gas mixture that is charged to heat exchanger section [g] via duct [22]. In heat exchanger section [g] the gas mixture that is charged via duct [14] is cooled down, while the hydrogen comprising gas mixture that is charged via duct [22] is heated up. The cooled down gas mixture comprising hydrogen, phenol, cyclohexanone and cyclohexanol is discharged from heat exchanger section [g] via duct [15]. Heat exchanger section [g] comprises one or more heat exchangers that are operated in parallel and/or in series. Optionally, heat exchanger section [g] is absent or by-passed (not shown in FIG. 2). The cooled down gas mixture comprising hydrogen, phenol, cyclohexanone and cyclohexanol is transported via duct [15] and is charged to heat exchanger section [h], wherein it is further cooled down and whereby optionally a fraction of the phenol, cyclohexanone and cyclohexanol is condensed. Optionally, as coolant a process flow from separation and purification section [II] or from cyclohexanol dehydrogenation reaction section [III] (not shown in FIG. 2) is used. Preferably, the process flow that is fed to the first distillation section in separation and purification section [II] is used as coolant, whereby that stream is heated up (not shown in FIG. 2). Heat exchanger section [h] comprises one or more heat exchangers that are operated in parallel and/or in series. Optionally, heat exchanger section [h] is absent or by-passed (not shown in FIG. 2).

The further cooled down mixture comprising hydrogen, phenol, cyclohexanone and cyclohexanol is transported via duct [16] and is charged to heat exchanger section [i], wherein it is further cooled down, whereby at least a fraction of the phenol, cyclohexanone and cyclohexanol is condensed in heat exchanger section [i]. Heat exchanger section [i] comprises one or more heat exchangers that are operated in parallel and/or in series. A mixture comprising hydrogen gas and liquid phenol, cyclohexanone and cyclohexanol is discharged from heat exchanger section [i] via duct [17] and is charged to gas-liquid separation section [j]. Gas-liquid separation section [j] comprises one or more gas-liquid separators that are operated in parallel and/or in series. A liquid mixture comprising phenol, cyclohexanone and cyclohexanol is discharged from gas-liquid separation section [j] via duct [18] and is charged to separation and purification section [H] shown in FIG. 3. A gas mixture comprising hydrogen is discharged from gas-liquid separation section [j] via duct [19] and is charged to compression section [k]. Compression section [k] comprises one or more devices to compress a gas mixture that are operated in parallel and/or in series. The compressed gas mixture that is discharged from compression section [i] via duct [20]. In general gas-liquid separation section [k] comprises a device, e.g. a wire-mesh demister, for removal of entrained droplets from the stream of gaseous components that is discharged. The compressed gas mixture that is discharged via duct [20] is split in a compressed gas mixture that is transported via duct [21] and in a compressed gas mixture that is transported via duct [22]. The compressed gas mixture that is transported via duct [22] is charged to heat exchanger section [g], where it is heated. Optionally, heat exchanger section [g] is absent or by-passed (not shown in FIG. 2). The heated gas mixture, recycled hydrogen gas, is discharged via duct [23] and is then combined with the hydrogen gas in duct [7].

The compressed gas mixture that is transported via duct [21] is charged to heat exchanger section [m], wherein the compressed gas mixture is cooled down. Liquid formed in heat exchanger section [m] is discharged via duct [25] and is charged to gas-liquid separation section [j]. The cooled down gas mixture obtained in heat exchanger section [m] is discharged via duct [24]. In general the gas mixtures discharged via duct [24] comprises hydrogen and one or more inert components, like nitrogen and/or methane. Optionally, this gas mixture discharged via duct [24] is used as fuel.

Figure 3:
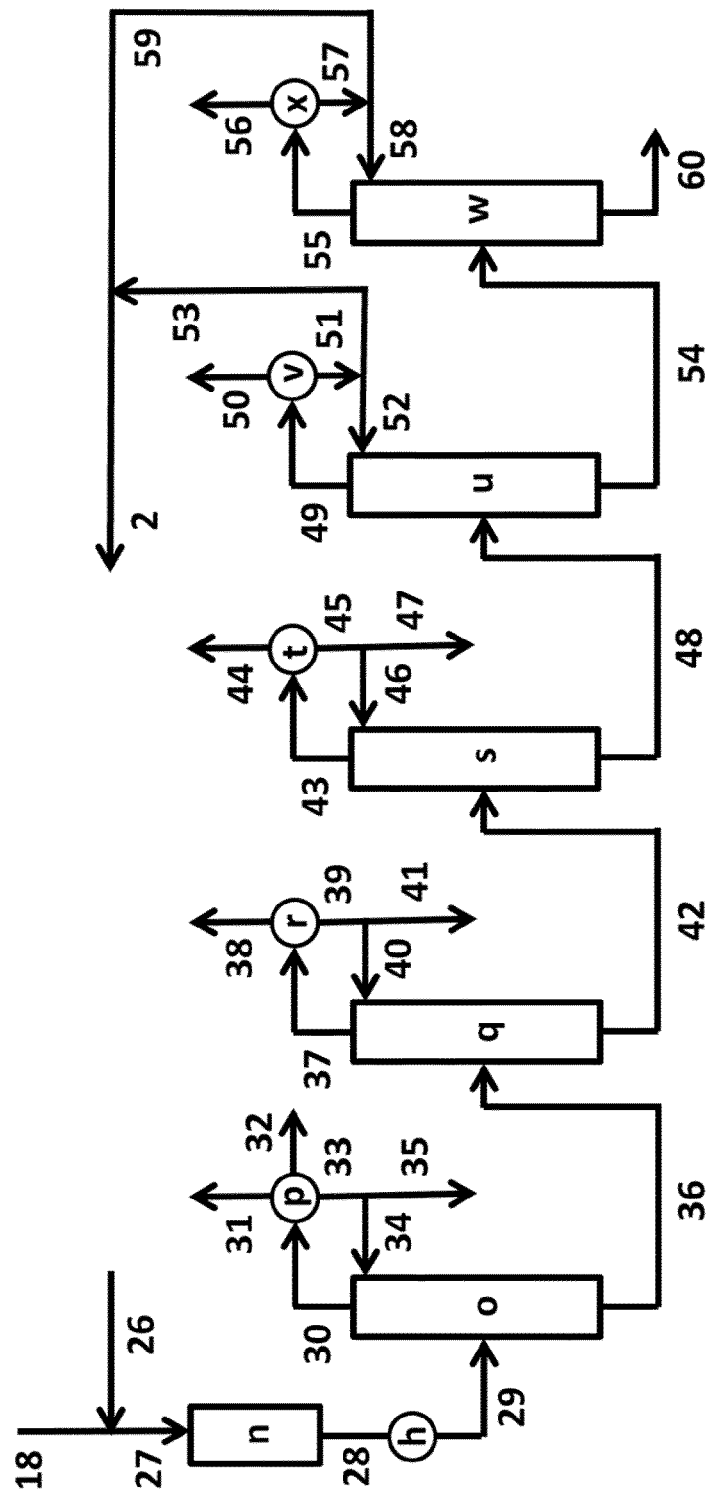
FIG. 3 illustrates schematically an embodiment of a separation and purification section [II] according to the invention.

In FIG. 3 a scheme of an embodiment according to the invention of the separation and purification section [II] is given.

The liquid mixture comprising phenol, cyclohexanone and cyclohexanol that is discharged from phenol hydrogenation reaction section [I] via duct [18] (FIG. 2) optionally may be combined with a liquid mixture comprising cyclohexanone and cyclohexanol that is discharged from cyclohexanol dehydrogenation reaction section [III] via duct [26] (FIG. 4) thereby forming a stream that flows via duct [27], that is charged to intermediate storage section [n].

Intermediate storage section [n] comprises one or more storage devices, e.g. vessels, tanks, containers. Optionally, intermediate storage section [n] is absent or is by-passed (not shown in FIG. 3). The liquid mixture comprising phenol, cyclohexanone and cyclohexanol that is discharged from intermediate storage section [n] via duct [28] is charged to heat exchanger section [h], where it is heated up. In heat exchanger section [h] the cooled down gas mixture comprising hydrogen, phenol, cyclohexanone and cyclohexanol that is transported via duct [15] (see FIG. 2) acts as heating medium. The heated up flow that is discharged from heat exchanger section [h] is charged to a first distillation section [o] via duct [29]. Heat exchanger section [h] comprises one or more heat exchangers that are operated in parallel and/or in series. Optionally, heat exchanger section [h] is absent or is by-passed (not shown in FIG. 3). Optionally, the liquid mixture transported through duct [29] is before being charged to the first distillation section [o] heated in another heat exchanger section (not shown in FIG. 3).

In the first distillation section [o] light components, e.g. benzene and water are removed from the feed that is charged via duct [29], whereas a mixture comprising cyclohexanone, phenol and cyclohexanol and heavy components is discharged from the first distillation section [o] as a bottom fraction via duct [36] and is charged to the second distillation section [q]. The first distillation section [o] comprises one or more distillation columns that are operated in series or in parallel. Preferably, the first distillation section [o] is operated at a pressure below 0.2 MPa. Preferably, the distillation column(s) in the first distillation section [o] is/are equipped with trays and/or packing, more preferably with trays. The distillation column(s) is/are equipped with one or more reboilers. Preferably, such a reboiler is steam driven. Top vapors are discharged from the first distillation section [o] via duct [30] and are condensed in condensation section [p]. In condensation section [p] three phases are obtained: a gaseous phase comprising hydrogen gas that is discharged via duct [31], an aqueous phase that is discharged via duct [32], and an organic phase that is discharged via duct [33]. Optionally, the gaseous phase comprising hydrogen gas that is discharged via duct [31] is sent to an incinerator (not shown in FIG. 3). Optionally, the aqueous phase that is discharged via duct [32] is sent to a waste water treatment system (not shown in FIG. 3). The organic phase that is discharged via duct [33] is split and a part is charged to the first distillation section [o] as reflux via duct [34] and another part is discharged as lights via duct [35]. Optionally, the lights that are discharged via duct [35] are charged to a buffer tank (not shown in FIG. 3). Optionally, the lights that are discharged via duct [35] are sent to an incinerator (not shown in FIG. 3). Condensation section [p] comprises one or more condensers that are operated in series or in parallel. Optionally, condensation section [p] comprises a separate liquid/liquid separator for separating the aqueous phase that is discharged via duct [32] and the organic phase that is discharged via duct [33].

In the second distillation section [q] cyclohexanone is removed from the feed that is charged via duct [36], whereas a mixture comprising phenol and cyclohexanol and heavy components is discharged from the second distillation section [q] as a bottom fraction via duct [42] and is charged to the third distillation section [s]. Second distillation section [q] comprises one or more distillation columns that are operated in series or in parallel. Preferably, the second distillation section [q] is operated at a pressure below 0.1 MPa. Preferably, the distillation column(s) in the second distillation section [q] is/are equipped with trays and/or packing, more preferably with packing. The distillation column(s) is/are equipped with one or more reboilers. Preferably, such a reboiler is steam driven.

Top vapors are discharged from the second distillation section [q] via duct [37] and are condensed in condensation section [r]. In condensation section [r] two phases are obtained: a gaseous phase comprising nitrogen gas and cyclohexanone vapors that is discharged via duct [38], and a cyclohexanone rich organic phase that is discharged via duct [39]. Optionally, the gaseous phase comprising nitrogen gas and cyclohexanone vapors that is discharged via duct [38] is sent to an incinerator (not shown in FIG. 3). The cyclohexanone rich organic phase that is discharged via duct [39] is split and a part is charged to the second distillation section [q] as reflux via duct [40] and another part is discharged as final product via duct [41]. In general, the final product that is discharged via duct [41] is charged to a final product tank (not shown in FIG. 3). Condensation section [q] comprises one or more condensers that are operated in series or in parallel. Optionally, condensation section [q] comprises a pump vessel from which the cyclohexanone rich organic phase is discharged via duct [39].

In the third distillation section [5] cyclohexanol is removed from the feed that is charged via duct [42], whereas a mixture comprising phenol and cyclohexanol and heavy components is discharged from the third distillation section [s] as a bottom fraction via duct [48] and is charged to the fourth distillation section [u]. Third distillation section [5] comprises one or more distillation columns that are operated in series or in parallel. Preferably, the third distillation section [5] is operated at a pressure below 0.1 MPa. Preferably, the distillation column(s) in the third distillation section [5] is/are equipped with trays and/or packing, more preferably with packing above the feeding point. The distillation column(s) is/are equipped with one or more reboilers. Preferably, such a reboiler is steam driven.

Figure 4:
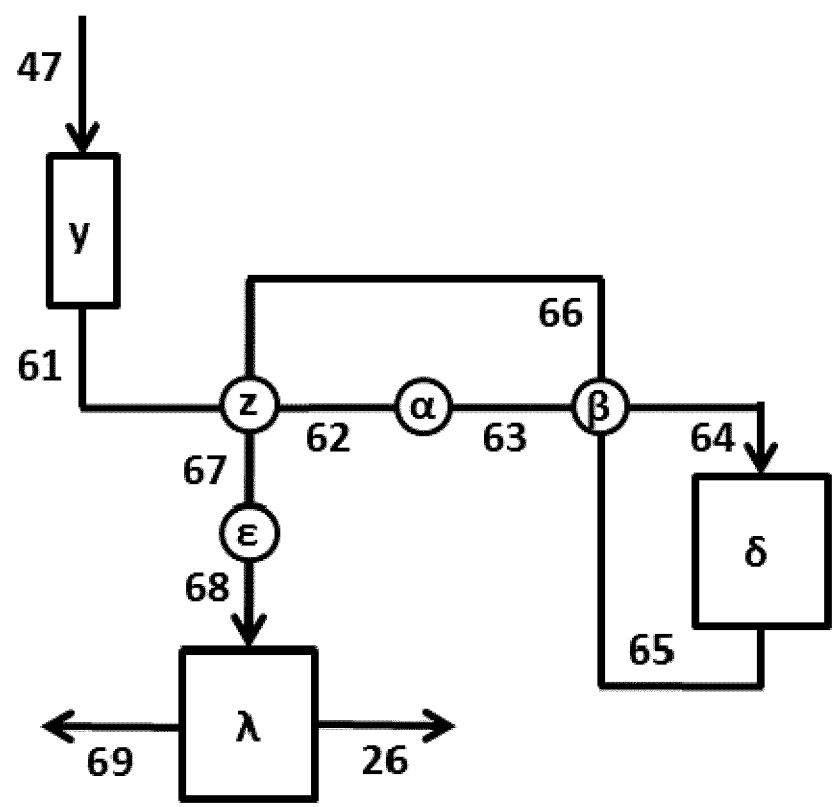
FIG. 4 illustrates schematically an embodiment of a cyclohexanol dehydrogenation reaction section [III] according to the invention.

Top vapors are discharged from the third distillation section [5] via duct [43] and are condensed in condensation section [t]. In condensation section [t] two phases are obtained: a gaseous phase comprising nitrogen gas and cyclohexanol vapors that is discharged via duct [44], and a cyclohexanol rich organic phase that is discharged via duct [45]. Optionally, the gaseous phase comprising nitrogen gas and cyclohexanol vapors that is discharged via duct [44] is sent to an incinerator (not shown in FIG. 3). The cyclohexanol rich organic phase that is discharged via duct [45] is split and a part is charged to the third distillation section [5] as reflux via duct [46] and another part is discharged via duct [47]. The cyclohexanol rich organic phase that is discharged via duct [47] is charged to cyclohexanol dehydrogenation reaction section [III] (FIG. 4). Optionally, a fraction or the whole cyclohexanol rich organic phase that is discharged via duct [47] is discharged to outside the process for the preparation and recovery of cyclohexanone from phenol (not shown in FIG. 3). Condensation section [t] comprises one or more condensers that are operated in series or in parallel. Optionally, condensation section [t] comprises a pump vessel from which the cyclohexanol rich organic phase is discharged via duct [45].

In the fourth distillation section [u] cyclohexanol and phenol are removed from the feed that is charged via duct [48], whereas a mixture comprising phenol and heavy components is discharged from the fourth distillation section [u] as a bottom fraction via duct [54] and is charged to the optional fifth distillation section [w]. Optionally, the mixture comprising phenol and heavy components that is discharged from the fourth distillation section [u] as a bottom fraction via duct [54] is discharged from the process (not shown in FIG. 3). Optionally, this mixture comprising phenol and heavy components that is discharged from the process via duct [54] is charged to a buffer tank (not shown in FIG. 3). Optionally, this mixture comprising phenol and heavy components that is discharged from the process via duct [54] is sent to an incinerator (not shown in FIG. 3).

Fourth distillation section [u] comprises one or more distillation columns that are operated in series or in parallel. Preferably, the fourth distillation section [u] is operated at a pressure below 0.1 MPa. Preferably, the distillation column(s) in the fourth distillation section [u] is/are equipped with trays and/or packing, more preferably with packing above feeding point and trays below the feeding point. The distillation column(s) are equipped with one or more reboilers. Preferably, such a reboiler is steam driven.

Top vapors are discharged from the fourth distillation section [u] via duct [49] and are condensed in condensation section [v]. In condensation section [v] two phases are obtained: a gaseous phase comprising nitrogen gas and phenol vapors that is discharged via duct [50], and a phenol and cyclohexanol rich phase that is discharged via duct [51]. Optionally, the gaseous phase comprising nitrogen gas and phenol vapors that is discharged via duct [50] is sent to an incinerator (not shown in FIG. 3). The phenol and cyclohexanol rich phase that is discharged via duct [51] is split and a part that is charged to the fourth distillation section [u] as reflux via duct [52] and another part is discharged via duct [53]. The phenol and cyclohexanol rich phase that is discharged via duct [53] is charged to phenol hydrogenation reaction section [I]. Optionally, a fraction or the whole phenol and cyclohexanol rich phase that is discharged via duct [53] is discharged to outside the process (not shown in FIG. 3). Condensation section [v] comprises one or more condensers that are operated in series or in parallel. Optionally, condensation section [v] comprises a pump vessel from which the phenol and cyclohexanol rich organic phase is discharged via duct [51].

In the optional fifth distillation section [w] phenol is removed from the feed that is charged via duct [54], whereas a mixture comprising phenol and heavy components is discharged from the fifth distillation section [w] as a bottom fraction via duct [60] and is discharged from the process. Optionally, this mixture comprising phenol and heavy components that is discharged from the process via duct [60] is charged to a buffer tank (not shown in FIG. 3). Optionally, this mixture comprising phenol and heavy components that is discharged from the process via duct [60] is sent to an incinerator (not shown in FIG. 3).

Fifth distillation section [w] comprises one or more distillation columns that are operated in series or in parallel. Preferably, the fifth distillation section [w] is operated at a pressure below 0.1 MPa. Preferably, the distillation column(s) in the fifth distillation section [w] is/are equipped with trays and/or packing, more preferably with packing above the feeding point and trays below the feeding point. The distillation column(s) is/are equipped with one or more reboilers. Preferably, such a reboiler is steam driven.

Top vapors are discharged from the fifth distillation section [w] via duct [55] and are condensed in condensation section [x]. In condensation section [x] two phases are obtained: a gaseous phase comprising nitrogen gas and phenol vapors that is discharged via duct [56], and a phenol rich organic phase that is discharged via duct [57]. Optionally, the gaseous phase comprising nitrogen gas and phenol vapors that is discharged via duct [56] is sent to an incinerator (not shown in FIG. 3). The phenol rich organic phase that is discharged via duct [57] is split and a part is charged to the fifth distillation section [w] as reflux via duct [58] and another part is discharged via duct [59]. The phenol rich organic phase that is discharged via duct [59] is charged to phenol hydrogenation reaction section [I] (FIG. 2). Optionally, a fraction or the whole phenol rich organic phase that is discharged via duct [59] is discharged to outside the process (not shown in FIG. 3). The phenol rich organic phase that is discharged via duct [59] and the phenol and cyclohexanol rich organic phase that is discharged via duct [53] are combined and are charged to phenol hydrogenation reaction section [I] via duct [2] (FIG. 2). Condensation section [x] comprises one or more condensers that are operated in series or in parallel. Optionally, condensation section [x] comprises a pump vessel from which the phenol rich organic phase is discharged via duct [57].

In FIG. 4 a scheme of an embodiment according to the invention of the cyclohexanol dehydrogenation reaction section [III] is given.

The cyclohexanol rich organic phase that is discharged from separation and purification section [II] via duct [47] (see also FIG. 3) is charged to intermediate storage section [y]. Intermediate storage section [y] comprises one or more storage devices, e.g. vessels, tanks, containers. Optionally, intermediate storage section [y] is absent or is by-passed (not shown in FIG. 4). The cyclohexanol rich organic phase that is discharged from an intermediate storage section [y] is charged to heat exchanger section [z] via duct [61], where it is heated up. In heat exchanger section [z] the cooled down mixture comprising hydrogen, cyclohexanone and cyclohexanol that is transported via duct [66] acts as heating medium. The heated up flow that is discharged from heat exchanger section [z] is charged to heat exchanger section [α] via duct [62]. Heat exchanger section [z] comprises one or more heat exchangers that are operated in parallel and/or in series. Optionally, heat exchanger section [z] is absent or is by-passed (not shown in FIG. 4). In heat exchanger section [α] the heated up flow that is discharged from heat exchanger section [z] via duct [62] is further heated up, whereby a further heated up flow is obtained that is discharged via duct [63]. Heat exchanger section [α] comprises one or more heat exchangers that are operated in parallel and/or in series. Preferably, heat exchanger section [α] is steam heated. Optionally, heat exchanger section [α] is absent or is by-passed (not shown in FIG. 4). The further heated up flow that is discharged from heat exchanger section [α] is charged to heat exchanger section [β] via duct [63], where it is even further heated up. In heat exchanger section [β] the mixture comprising hydrogen, cyclohexanone and cyclohexanol that is transported via duct [65] acts as heating medium. The even further heated up flow that is discharged from heat exchanger section [β] is charged to cyclohexanol dehydrogenation reactor section [δ] via duct [64]. Heat exchanger section [β] comprises one or more heat exchangers that are operated in parallel and/or in series. Optionally, heat exchanger section [β] is absent or is by-passed (not shown in FIG. 4).

In cyclohexanol dehydrogenation reactor section [δ] a part of the cyclohexanol present in the even further heated up flow that is charged via duct [64] is converted into cyclohexanone and hydrogen. Because this dehydrogenation reaction of cyclohexanol is endothermic the cyclohexanol dehydrogenation reactor section [δ] is heated. In the general heating of this cyclohexanol dehydrogenation reactor section [δ] is done with flue gases, thermic oil, liquid metals or steam as heating medium. Preferably, the heating of this cyclohexanol dehydrogenation reactor section [δ] is done with steam or thermic oil as heating medium, more preferably with steam. Cyclohexanol dehydrogenation reactor section [δ] comprises one or more dehydrogenation reactors that are operated in parallel and/or in series. A dehydrogenation reactor may in particular be any type of reactor suitable for dehydrogenation of the compound to be dehydrogenated, in particular any reactor suitable for the dehydrogenation of cyclohexanol. In particular, the reactor may be selected from packed bed reactors, slurry reactors, shell and tube type heat exchange reactors. Most preferably, the dehydrogenation according to the invention is carried out in a shell and tube type heat exchange reactor with dehydrogenation catalyst in the tubes and the heating medium outside the tubes. Most preferably, both the feed and the discharge of the cyclohexanol dehydrogenation reactor section [δ] are in the gaseous state.

A mixture comprising hydrogen, cyclohexanone and cyclohexanol is discharged from cyclohexanol dehydrogenation reactor section [δ] and is charged to heat exchanger section [β] via duct [65]. In heat exchanger section [β] the mixture comprising hydrogen, cyclohexanone and cyclohexanol is cooled down whereby a cooled down mixture comprising hydrogen, cyclohexanone and cyclohexanol is obtained that is discharged via duct [66]. This cooled down mixture comprising hydrogen, cyclohexanone and cyclohexanol is charged to heat exchanger section [z] via duct [66]. In heat exchanger section [z] the cooled down mixture comprising hydrogen, cyclohexanone and cyclohexanol is further cooled down whereby a further cooled down mixture comprising hydrogen, cyclohexanone and cyclohexanol is obtained that is discharged via duct [67]. This further cooled down mixture comprising hydrogen, cyclohexanone and cyclohexanol is charged to heat exchanger section [ε] via duct [67]. In heat exchanger section [ε] the further cooled down mixture comprising hydrogen, cyclohexanone and cyclohexanol is further cooled down whereby an even further cooled down mixture comprising hydrogen, cyclohexanone and cyclohexanol is obtained that is discharged via duct [68]. Preferably, this even further cooled down mixture comprising hydrogen, cyclohexanone and cyclohexanol comprises consists of a liquid phase comprising mainly cyclohexanone and cyclohexanol, and a gaseous phase comprising hydrogen. This even further cooled down mixture comprising hydrogen, cyclohexanone and cyclohexanol is charged to gas-liquid separation section [λ] via duct [68]. Gas-liquid separation section [λ] comprises one or more gas-liquid separators that are operated in parallel and/or in series. A liquid mixture comprising mainly cyclohexanone and cyclohexanol is discharged from gas-liquid separation section [λ] via duct [26] and is charged to separation and purification section [II] (see also FIG. 3). A gas mixture comprising hydrogen is discharged from gas-liquid separation section [λ] via duct [69]. Optionally, the gas mixture comprising hydrogen that is discharged via duct [69] is sent to an incinerator (not shown in FIG. 4). Optionally, the gas mixture comprising hydrogen that is discharged via duct [69] is sent to phenol hydrogenation reaction section [I] (not shown in FIG. 4).

The present invention is illustrated by, but not intended to be limited to, the following examples:

Example 1 describes a chemical plant for the preparation and recovery of cyclohexanone from phenol with a phenol hydrogenation catalyst that has been used for a period of about 1 week.

Example 2 describes a chemical plant for the preparation and recovery of cyclohexanone from phenol with a phenol hydrogenation catalyst that has been used for a period of about 9 months.

EXAMPLE 1

An industrial scale chemical plant with a hourly capacity of about 12.5 tons cyclohexanone per hour, that is operated in a continuous mode, for the preparation and recovery of cyclohexanone from phenol feedstock, comprising:
  a phenol hydrogenation reaction section [I],
  a separation and purification section [II], and
  a cyclohexanol dehydrogenation reaction section [III] as described before and as depicted in FIGS. 1, 2, 3 and 4 was used.

The phenol hydrogenation reaction section [I] comprised:
  steam heated heat exchanger section [a];
  steam heated evaporation section [b];
  steam heated heat exchanger section [c];
  hydrogen purification unit [d], in which CO was catalytically converted and $H_2S$ was removed by an adsorbent;
  steam heated heat exchanger section [e];
  phenol hydrogenation section [f], comprising two shell and tube types hydrogenation reactors for phenol hydrogenation in the vapour phase that was operated in parallel and water was used as coolant was evaporated to form steam;

heat exchanger section [g];
heat exchanger section [h], in which heat was exchanged between the phenol hydrogenation reaction section [I] and the separation and purification section [II];
water cooled heat exchanger section [i];
gas-liquid separation section [j];
compression section [k];
heat exchanger section [m]; and
ducts [1] to [25]
which were all in use during normal operation of the plant.

Fresh phenol was charged to phenol hydrogenation reaction section [I] via duct [1]. As fresh hydrogen gas a gas mixture comprising about 94 vol. % hydrogen and about 6 vol. % nitrogen was charged to the phenol hydrogenation reaction section [I] via duct [5]. Under normal operation conditions, both the CO content and the $H_2S$ content of this fresh hydrogen were each below 1 ppm. The ratio of the amount of steam that was added via duct [12] to the stream in duct [11] to the amount of fresh phenol was about 1 wt. %. As hydrogenation catalyst $Pd/Al_2O_3$ (1 wt. %) with 1 wt. % Na (as $NaHCO_3$) added as promoter was applied.

The separation and purification section [II] comprised:
intermediate storage section [n];
heat exchanger section [h], in which heat was exchanged between the phenol hydrogenation reaction section [I] and the separation and purification section [II];
first distillation section [o];
condensation section [p];
second distillation section [q];
condensation section [r];
third distillation section [s];
condensation section [t];
fourth distillation section [u];
condensation section [v];
fifth distillation section [w];
condensation section [x]; and
ducts [2], [18] and [26] to [60];
which were all in use during normal operation of the plant.

All distillation columns in the first distillation section [o], the second distillation section [q], the third distillation section [s], the fourth distillation section [u], and the fifth distillation section [w] were equipped with steam driven reboilers.

The cyclohexanol dehydrogenation reaction section [III] comprised:
intermediate storage section [y];
heat exchanger section [z];
steam heated heat exchanger section [α];
heat exchanger section [β];
cyclohexanol dehydrogenation reactor section [δ], comprising a shell and tube type reactor;
water cooled heat exchanger section [ε];
gas-liquid separation section [λ]; and
ducts [26], [47] and [61] to [69];
which were all in use during normal operation of the plant.

The heating medium applied in the cyclohexanol dehydrogenation reactor was steam.

After a period of about 1 week after start-up of the chemical plant for the preparation and recovery of cyclohexanone from phenol with fresh phenol hydrogenation catalyst the following results were obtained:
The final product, cyclohexanone, that was discharged via duct [41] had a cyclohexanol content of about 500 ppm (weight/weight) [99.95 wt. %].

The molar ratio of cyclohexanone over phenol that was charged to the phenol hydrogenation reactors was about 0.04.
The molar ratio of cyclohexanol over phenol that was charged to the phenol hydrogenation reactors was about 0.005.
The molar ratio of cyclohexanone over cyclohexanol in the hydrogenated product stream in duct [14] was greater than 100.
The molar ratio of cyclohexanone over cyclohexanol in the hydrogenated product stream discharged from the phenol hydrogenation reaction section [I] via duct [18] was greater than 100.
The molar ratio of cyclohexanone over phenol in the hydrogenation product stream in duct [14] was greater than 100.
The molar ratio of cyclohexanone over phenol in the hydrogenated product stream discharged from the phenol hydrogenation reaction section [I] via duct [18] was greater than 100.
The molar fraction of fresh phenol feedstock that was converted into cyclohexanone was greater than 99%.

The net energy consumption is about 0.7 MJ per kg produced cyclohexanone and the net steam consumption was about 0.3 kg steam per kg produced cyclohexanone. Whereby the energy consumers were:
steam heated heat exchanger section [a];
steam heated evaporation section [b];
steam heated heat exchanger section [c];
steam heated heat exchanger section [e];
steam heated reboilers of the first distillation section [o], of the second distillation column [q], of the third distillation column [s], of the fourth distillation column [u], and of the fifth distillation column [w];
steam heated heat exchanger section [α]; and
steam heated cyclohexanol dehydrogenation reactor section [δ]; and the energy producers were:
two shell and tube type hydrogenation reactors in phenol hydrogenation section [f].

All above mentioned energy consumers are also steam consumers. All above mentioned energy producers are also steam producers.

EXAMPLE 2

The preparation and recovery of cyclohexanone from phenol was carried out in the same chemical plant as described in Example 1, except that now the phenol hydrogenation catalyst has been used for a period of time of about 9 months instead of about 1 week. It is well known that phenol hydrogenation catalysts shown aging behavior, resulting in reduced selectivity and activity over time.

Now the following results were obtained:
The final product, cyclohexanone, that was discharged via duct [41] had a cyclohexanol content of about 500 ppm (weight/weight).
The molar ratio of cyclohexanone over phenol that was charged to the phenol hydrogenation reactors was about 0.04.
The molar ratio of cyclohexanol over phenol that was charged to the phenol hydrogenation reactors was about 0.024.
The molar ratio of cyclohexanone over cyclohexanol in the hydrogenation product stream in duct [14] was about 12.

The molar ratio of cyclohexanone over cyclohanol in the hydrogenated product stream discharged from the phenol hydrogenation reaction section [I] via duct [18] was about 12.

The molar ratio of cyclohexanone over phenol in the hydrogenation product stream in duct [14] was about 14.

The molar ratio of cyclohexanone over phenol in the hydrogenated product stream discharged from the phenol hydrogenation reaction section [I] via duct [18] was about 14.

The molar fraction of fresh phenol feedstock that is converted into cyclohexanone was greater than 99%.

The net energy consumption is about 1.6 MJ per kg produced cyclohexanone and the net steam consumption was about 0.7 kg steam per kg produced cyclohexanone. Whereby the energy consumers and the steam consumers and energy producers and steam producers were the same as in Example 1.

In both EXAMPLE 1 and EXAMPLE 2
the per-pass selectivity in the phenol hydrogenation reaction section was more than 93%, and
the per-pass phenol conversion in the phenol hydrogenation section was more than 91%.

In both EXAMPLE 1 and EXAMPLE 2 more than 80% of the reaction heat produced in the phenol hydrogenation reaction section was applied for the production of steam.

The invention claimed is:

1. An industrial scale continuous process for the production and recovery of cyclohexanone from phenol and hydrogen, said process comprising:
   I) hydrogenating phenol in a phenol hydrogenation reactor in a phenol hydrogenation reaction section [I] with gaseous hydrogen, in the presence of a catalyst, comprising at least one of platinum and palladium metal whereby reaction heat is produced and from which a hydrogenated product stream is discharged;
   II) separating cyclohexanone from said hydrogenated product stream in a separation and purification section [II] by multiple-steps comprising:
      i. removing in a first distillation section, components with a boiling point lower than cyclohexanone;
      ii. removing in a second distillation section cyclohexanone;
      iii. removing in a third distillation section a cyclohexanol rich phase; and
      iv. removing in a fourth distillation section a mixture comprising phenol and cyclohexanol;
   wherein said cyclohexanone has a cyclohexanol content below 5000 ppm (weight/weight);
   wherein at least some of the reaction heat produced in the phenol hydrogenation reaction section [I] is applied for the production of steam; and
   wherein the mixture comprising phenol and cyclohexanol that is removed in step iv) is charged to the phenol hydrogenation reaction section [I];
   characterized in that conditions a) and b) apply:
      a. the molar ratio of cyclohexanone to phenol that is charged to said phenol hydrogenation reactor is from 0.02 to 0.10; and
      b. the molar ratio of cyclohexanol to phenol that is charged to said phenol hydrogenation reactor is from 0.001 to 0.10.

2. The process according to claim 1, in which said process further comprises dehydrogenating cyclohexanol into cyclohexanone and hydrogen in a cyclohexanol dehydrogenation reaction section [III].

3. The process according to claim 1, in which the molar ratio of cyclohexanone over cyclohexanol in the hydrogenated product stream discharged in step I) is greater than 10.

4. The process according to claim 1, in which the molar ratio of cyclohexanone over phenol in the hydrogenation product stream discharged in step I) is greater than 10.

5. The process according to claim 2, in which hydrogen produced in the cyclohexanol dehydrogenation reaction section [III] is charged to the phenol hydrogenation reaction section [I].

6. The process according to claim 1, in which phenol is hydrogenated in a vapour phase process.

7. The process according to claim 1, wherein the net steam consumption is less than 1.5 kg steam per kg produced cyclohexanone.

8. The process according to claim 1, wherein the net energy consumption is less than 3 MJ per kg produced cyclohexanone.

9. The process according to claim 1, wherein said cyclohexanone has a cyclohexanol content below 2000 ppm (weight/weight).

10. The process according to claim 1, wherein the catalyst comprises palladium on an alumina support and a promoter comprising a Na-comprising salt.

11. The process according to claim 1, wherein the catalyst comprises 1 wt. % palladium on an alumina support, and a promoter comprising 1 wt. % Na (as $NaHCO_3$).

12. The process according to claim 1, wherein more than 98% (mol/mol) of the phenol that is charged to the process is converted into cyclohexanone.

13. The process according to claim 1, wherein the phenol hydrogenation reaction section [I] comprises a per pass selectivity of more than 92% and a per-pass phenol conversion more than 90%.

14. An industrial scale continuous chemical plant for the production and recovery of cyclohexanone from phenol and hydrogen, said plant comprising:
   I) a phenol hydrogenation reaction section [I] comprising a phenol hydrogenation reactor in which phenol is hydrogenated with gaseous hydrogen, in the presence of a catalyst comprising at least one of platinum and palladium metal, whereby reaction heat is produced and from which a hydrogenated product stream is discharged;
   II) a separation and purification section [II] in which cyclohexanone is separated from said hydrogenated product stream by multiple-steps comprising:
      i. a first distillation section, in which components with a boiling point lower than cyclohexanone are removed;
      ii. a second distillation section, in which cyclohexanone is removed;
      iii. a third distillation section, in which a cyclohexanol rich phase is removed; and
      iv. a fourth distillation section, in which a mixture comprising phenol and cyclohexanol is removed;
   wherein said cyclohexanone has a cyclohexanol content below 5000 ppm (weight/weight);
   wherein at least some of the reaction heat produced in the phenol hydrogenation reaction section [I] is applied for the production of steam; and
   wherein the mixture comprising phenol and cyclohexanol that is removed in step iv) is charged to the phenol hydrogenation reaction section [I];

characterized in that conditions a) and b) apply:
  a. the molar ratio of cyclohexanone to phenol that is charged to said phenol hydrogenation reactor is from 0.02 to 0.10; and
  b. the molar ratio of cyclohexanol to phenol that is charged to said phenol hydrogenation reactor is of from 0.001 to 0.10.

* * * * *